United States Patent
Ringlien

(12) 
(10) Patent No.: US 6,256,095 B1
(45) Date of Patent: Jul. 3, 2001

(54) CONTAINER SEALING SURFACE AREA INSPECTION

(75) Inventor: James A. Ringlien, Maumee, OH (US)

(73) Assignee: Owens-Brockway Glass Container Inc., Toledo, OH (US)

( * ) Notice: Subject to any disclaimer, the term of this patent is extended or adjusted under 35 U.S.C. 154(b) by 0 days.

(21) Appl. No.: 09/488,843

(22) Filed: Jan. 21, 2000

(51) Int. Cl.$^7$ .................................................. G01N 21/00
(52) U.S. Cl. ..................................... 356/239.4; 356/240.1
(58) Field of Search ........................... 356/239.4, 239.5, 356/239.6, 240.1; 250/223 B, 225, 562, 572, 206

(56) References Cited

U.S. PATENT DOCUMENTS

| | | |
|---|---|---|
| 3,313,409 | 4/1967 | Johnson . |
| 3,735,144 * | 5/1973 | Babunovic et al. ................ 356/240 |
| 3,778,617 * | 12/1973 | Calnoun ................................ 250/206 |
| 3,788,741 | 1/1974 | Buechler . |
| 3,880,750 | 4/1975 | Butler et al. . |
| 4,198,164 | 4/1980 | Cantor . |
| 4,230,219 | 10/1980 | Pezzin et al. . |
| 4,376,951 | 3/1983 | Mayazawa . |
| 4,378,493 | 3/1983 | Dorf et al. . |
| 4,386,828 | 6/1983 | Hirose . |
| 4,476,533 | 10/1984 | Daudt . |
| 4,488,648 | 12/1984 | Claypool . |
| 4,491,728 | 1/1985 | Fischer . |
| 4,492,476 | 1/1985 | Miyazawa . |
| 4,526,443 | 7/1985 | Hirose . |
| 4,694,158 | 9/1987 | Leser . |
| 4,697,076 | 9/1987 | Yoshida . |
| 4,701,612 | 10/1987 | Sturgill . |
| 4,725,856 | 2/1988 | Fujikura . |
| 4,758,084 | 7/1988 | Tokumi et al. . |
| 4,762,544 | 8/1988 | Davey . |

(List continued on next page.)

FOREIGN PATENT DOCUMENTS

| | | |
|---|---|---|
| 0192487 | 8/1986 | (EP) . |
| 0331290 | 9/1989 | (EP) . |
| 0698776 | 2/1996 | (EP) . |
| 0833126 | 4/1996 | (EP) . |
| 0764846 | 3/1997 | (EP) . |
| 2112931 | 7/1983 | (GB) . |
| 59-65243 | 4/1984 | (JP) . |
| 61-193009 | 8/1986 | (JP) . |
| 62-138709 | 6/1987 | (JP) . |
| 63-228049 | 9/1988 | (JP) . |
| 8122276 | 5/1996 | (JP) . |
| 8136224 | 5/1996 | (JP) . |
| 8278113 | 10/1996 | (JP) . |
| 9101128 | 4/1997 | (JP) . |

*Primary Examiner*—Frank G. Font
*Assistant Examiner*—Sang H. Nguyen

(57) ABSTRACT

Apparatus for inspecting the sealing surface area of a container finish that includes a light source positioned to direct a collimated line-shaped light beam (i.e., having a length dimension many times a width dimension) onto the sealing surface area of a container. The line-shaped light beam at the container sealing surface area has a long dimension orthogonal to the container axis, and a narrow dimension tangential to the container axis. A light sensor is disposed to receive portions of the line-shaped light beam reflected from the sealing surface area, and provides an electrical output signal that varies with height or level of the sealing surface area with respect to the light source and sensor. A lens system is disposed to direct onto the light sensor only light energy reflected from the container sealing surface area in planes parallel to the common plane of the container axis and the sensor. The lens system and sensor together comprise a full imaging system for light energy reflected from the sealing surface in planes parallel to the common plane of the container axis and the sensor, but which is substantially immune from stray reflections, including reflections from other points on the container, that are not parallel to this plane.

8 Claims, 4 Drawing Sheets

U.S. PATENT DOCUMENTS

| | | |
|---|---|---|
| 4,792,695 | 12/1988 | Blandford . |
| 4,811,251 | 3/1989 | Minato . |
| 4,816,668 | 3/1989 | Williams et al. . |
| 4,868,404 | 9/1989 | Hajime . |
| 4,900,916 | 2/1990 | Cormack . |
| 4,906,098 | 3/1990 | Thomas et al. . |
| 4,914,289 * | 4/1990 | Nguyen et al. ............ 250/223 B |
| 4,929,828 | 5/1990 | Claypool . |
| 4,945,228 | 7/1990 | Juvinall et al. . |
| 4,958,223 | 9/1990 | Juvinall et al. . |
| 5,008,743 | 4/1991 | Katzir et al. . |
| 5,020,908 | 6/1991 | Hermann . |
| 5,085,516 | 2/1992 | Bertrand et al. . |
| 5,200,801 | 4/1993 | Juvinall et al. . |
| 5,249,034 | 9/1993 | Minato . |
| 5,291,271 | 3/1994 | Juvinall et al. . |
| 5,305,391 | 4/1994 | Gomibuchi . |
| 5,381,235 | 1/1995 | Inoue et al. . |
| 5,461,228 | 10/1995 | Kirkman et al. . |
| 5,489,987 | 2/1996 | Ringlien . |
| 5,592,286 * | 1/1997 | Fedor ............................ 356/240.1 |
| 5,610,391 | 3/1997 | Ringlien . |
| 5,896,195 | 4/1999 | Juvinall et al. . |
| 6,025,909 * | 2/2000 | Juvinall et al. ............... 356/239.4 |

* cited by examiner

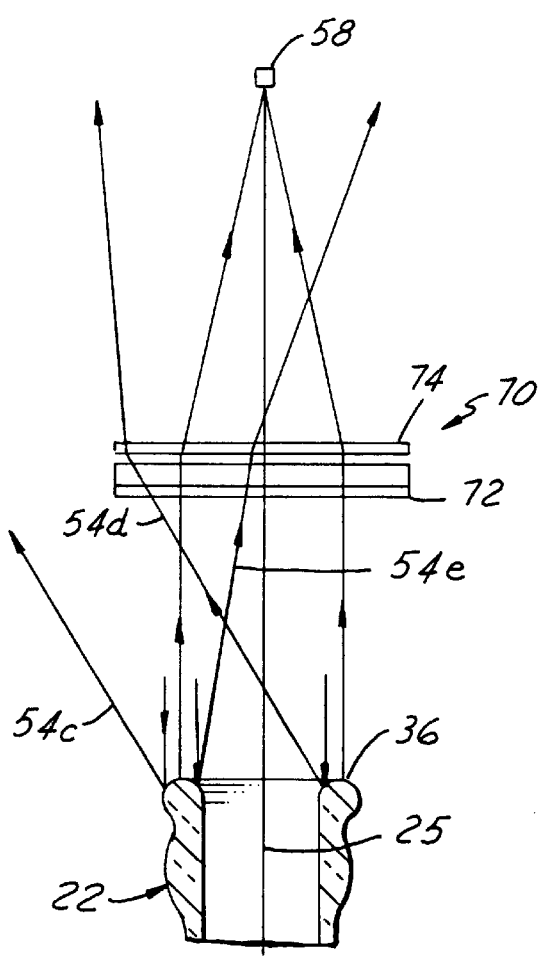
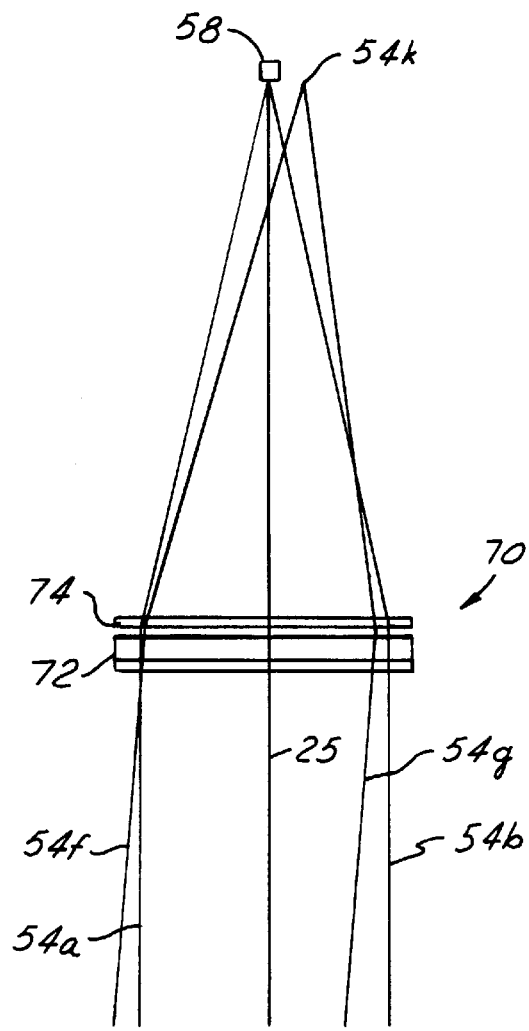
FIG. 7
FIG. 8

CONTAINER SEALING SURFACE AREA INSPECTION

The present invention is directed to inspection of containers, and more particularly to a method and apparatus for detecting commercial variations at the sealing surface area of a container.

BACKGROUND AND OBJECTS OF THE INVENTION

U.S. Pat. No. 3,313,409 discloses an apparatus for inspecting glass containers in which a starwheel conveys containers in sequence through a series of inspection stations. At one of the inspection stations, selected dimensional parameters of each container are inspected by contacting the container with rollers coupled to sensors, and rotating the container about its central axis so that the sensors provide output signals that vary as a function of variations of the container parameters. Specifically, container height, sealing surface warp and dip, and cocked orientation of the container finish are measured by rollers that engage the container sealing surface as the container rotates. The rollers are coupled to LVDT sensors that provide analog electrical signals indicative of deviations or variations in height (level) at the sealing surface. These signals are fed to appropriate electronics to energize a reject plunger for separating a container from the conveyor line if the measurement signals depart from desired standards and specifications. The rollers in contact with the container sealing surface are subject to mechanical wear, and can cause contamination at the sealing surface. Furthermore, the size of the rollers limits the size of containers in connection with which they may be employed, and the size (resolution) of height variations that can be detected. The moving parts require maintenance and repair. Furthermore, the roller construction is not adapted to measure height of any wire-edge or over-press within the sealing surface lip.

U.S. Pat. No. 4,945,228 discloses an apparatus for inspecting the sealing surface area of a container finish that includes a light source positioned to direct light energy onto the container sealing surface as the container is held in stationary position and rotated about its central axis. A camera, which includes a linear array or matrix (area) array of light sensitive elements, is positioned and oriented with respect to the container axis of rotation to receive light energy reflected by the sealing surface, with the camera having an effective field of view limited to an angular portion less than the entire circumference of the container sealing surface. The camera array is scanned at increments of container rotation to develop information indicative of intensity of light at each array element as a function of such increments, and commercial variations at the container sealing surface are detected as a function of such information. The apparatus so disclosed is well adapted to detect commercial variations that affect reflectivity of the container sealing surface, such as line-over-finish variations, blisters, stones and a dirty container finish. However, the apparatus so disclosed is not adapted to measure dimensional parameters of the container finish, such as height of the container sealing surface, warp, dip or cock at the container sealing surface, and/or height of any wire-edge or over-press at the sealing surface (The term "commercial variations" refers to variations that can affect commercial acceptability of the container. The term "sealing surface area" refers not only to the sealing surface itself, but also to any wire-edge, over-press or other commercial variation at the sealing surface.)

U.S. Pat. No. 5,489,987 discloses an apparatus for inspecting the sealing surface area of containers that includes a light source positioned to direct a narrow beam of light energy at an acute angle onto the sealing surface area of a container as the container is rotated about its central axis. A light sensor is disposed to receive the narrow beam of light energy reflected from the sealing surface area, and provides an output signal that varies as a function of position of incidence of the reflected light beam on the sensor. That is, the reflected light beam is incident on the sensor at a position that varies with height or level of the sealing surface with respect to the light source and sensor, and the sensor is characterized by providing an electrical output signal that varies as a function of position of incidence of the reflected light beam on the sensor. Variations in height at the sealing surface area are detected as a function of the sensor output signal. In one embodiment, light source/sensor pairs are disposed on diametrically opposed sides of the container axis, and warp, dip and/or cock at the sealing surface of the container is detected as a combined function of variations in position of incidence of the reflected light beams on the sensors as the container rotates.

U.S. Pat. No. 5,896,195 discloses an apparatus for inspecting the sealing surface area of a container finish that includes a structured light source positioned to direct a collimated-line shaped light beam onto the sealing surface area of a container as the container is moved, either laterally or rotationally, relative to the light source. The line-shaped beam at the container sealing surface area has a long dimension orthogonal to the container axis that extends chordally across the sealing surface area, and a narrow dimension tangential to the container axis. A light sensor is disposed to receive portions of the line-shaped light beam reflected from the sealing surface area, and provides an electrical output signal that varies with height or level of the sealing surface with respect to the light source and sensor. The sensor is coupled to associated electronics for providing information indicative of sealing surface height. The elongated dimension of the line-shaped beam at the container sealing surface area accommodates wobble or misalignment of the sealing surface area with respect to the light source and sensor. Furthermore, the elongated radial dimension of the line-shaped light beam at the container sealing surface area produces a reflection on the sensor from any wire-edge or over-press within the container mouth, thus producing at the sensor information indicative of both existence and height of any such wire-edge or over-press.

Although the apparatus disclosed in the noted patents overcome problems theretofore extant in the art, further improvements remain desirable. For example, the apparatus disclosed in U.S. Pat. No. 5,489,987 employs narrow field detectors mounted on one or both sides of the sealing surface, for which placement is critical and which can fail to receive a signal from the container if the container moves out of alignment. The apparatus disclosed in U.S. Pat. No. 5,896,195 overcomes this problem, but presents an additional problem in which it is at least possible to receive stray reflections, such as from chordally opposite areas of the sealing surface, that can confuse or obscure height measurement on one side of the sealing surface. It is therefore a general object of the present invention to provide an improved apparatus and method for inspecting the sealing surface area of containers for unacceptable commercial variations. Another and more specific object of the present invention is to provide an apparatus and method of the described character that are adapted to inspect the sealing surface area of a container for multiple types of variations in a single operation and at a single inspection station. A further object of the present invention is to provide a method and apparatus of the described character for inspecting both optical and dimensional characteristics of the sealing surface area of a container finish.

It is another object of the present invention to provide an apparatus and method for measuring or determining dimensional characteristics of a container finish, particularly a container sealing surface area, of the type disclosed in the above-noted U.S. Pat. No. 5,489,987, in which the measurement process is characterized by improved immunity to positional variations or wobble at the container sealing surface, and to stray reflections within the measurement area. Another object of the present invention is to provide a method and apparatus of the described character that attain the foregoing objective while being economical to implement and reliable over an extended operating lifetime. A further object of the present invention is to provide a method and apparatus of the described character that, in alternative embodiments, may be implemented at either the hot end or the cold end of a glassware manufacturing system.

SUMMARY OF THE INVENTION

Apparatus for inspecting the sealing surface area of a container finish in accordance with one aspect of the present invention includes a light source positioned to direct a collimated line-shaped light beam (i.e., having a length dimension many times a width dimension) onto the sealing surface area of a container. The line-shaped light beam at the container sealing surface area has a long dimension orthogonal to the container axis, and a narrow dimension tangential to the container axis. A light sensor is disposed to receive portions of the line-shaped light beam reflected from the sealing surface area, and provides an electrical output signal that varies with height or level of the sealing surface area with respect to the light source and sensor. A lens system is disposed to direct onto the light sensor only light energy reflected from the container sealing surface area in planes parallel to the common plane of the container axis and the sensor. The lens system and sensor together comprise a full imaging system for light energy reflected from the sealing surface in planes parallel to the common plane of the container axis and the sensor, but which is substantially immune from stray reflections, including reflections from other points on the container, that are not parallel to this plane.

The sensor is coupled to associated electronics for providing information indicative of sealing surface height. In the preferred embodiments, multiple images are obtained at the sensor from different portions of the sealing surface, either by moving the sealing surface area relative to the light source and sensor between images, or by employing multiple laser lines and reflections from the sealing surface. The elongated dimension of the line-shaped light beam at the container sealing surface accommodates wobble or misalignment at the sealing surface with respect to the light source and sensor. Furthermore, the elongated radial dimension of the line-shaped beam at the container sealing surface produces a reflection on the sensor from the wire-edge within the container mouth, thus producing at the sensor information indicative of both existence and height of any such wire-edge, and whether height of the wire-edge exceeds height of the sealing surface—i.e., an over-press.

The light source and sensor in the preferred embodiments of the invention are disposed above the sealing surface area of the container, and are oriented with respect to each other and with respect to the container sealing surface area such that portions of the light beam incident on and reflected from the container sealing surface area are nominally at a 90° angle with respect to each other, and nominally in a plane perpendicular to the sealing surface. (The term "nominal" refers to conditions that prevail at the ideal or design height and orientation of the sealing surface, any departure from such ideal height and orientation due to a short container or wobble at the container finish potentially causing minor departure from the "nominal" reflected beam orientation and angle.) The light source and sensor are disposed in a plane nominally parallel to the container axis and perpendicular to the sealing surface. The light sensor in the preferred embodiments of the invention includes a linear array sensor, and the lens system direct two spots of light onto the linear array sensor from the two sides of the finish sealing surface. If the spots are coincident, the two sides of the finish are at the same height. If the spots of light are at different locations on the sensor array, they must have come from locations on the finish that are at different heights—i.e., the finish is cocked, warped, etc. The absolute height of the container sealing surface can be measured since the position of the reflected light on the array is a measure of the height of the plane of the sealing surface.

BRIEF DESCRIPTION OF THE DRAWINGS

The invention, together with additional objects, features and advantages thereof, will be best understood from the following description, the appended claims and the accompanying drawings in which:

FIGS. 4–8 are schematic light ray diagrams that illustrate operation of the invention.

DETAILED DESCRIPTION OF PREFERRED EMBODIMENTS

Figure 1:
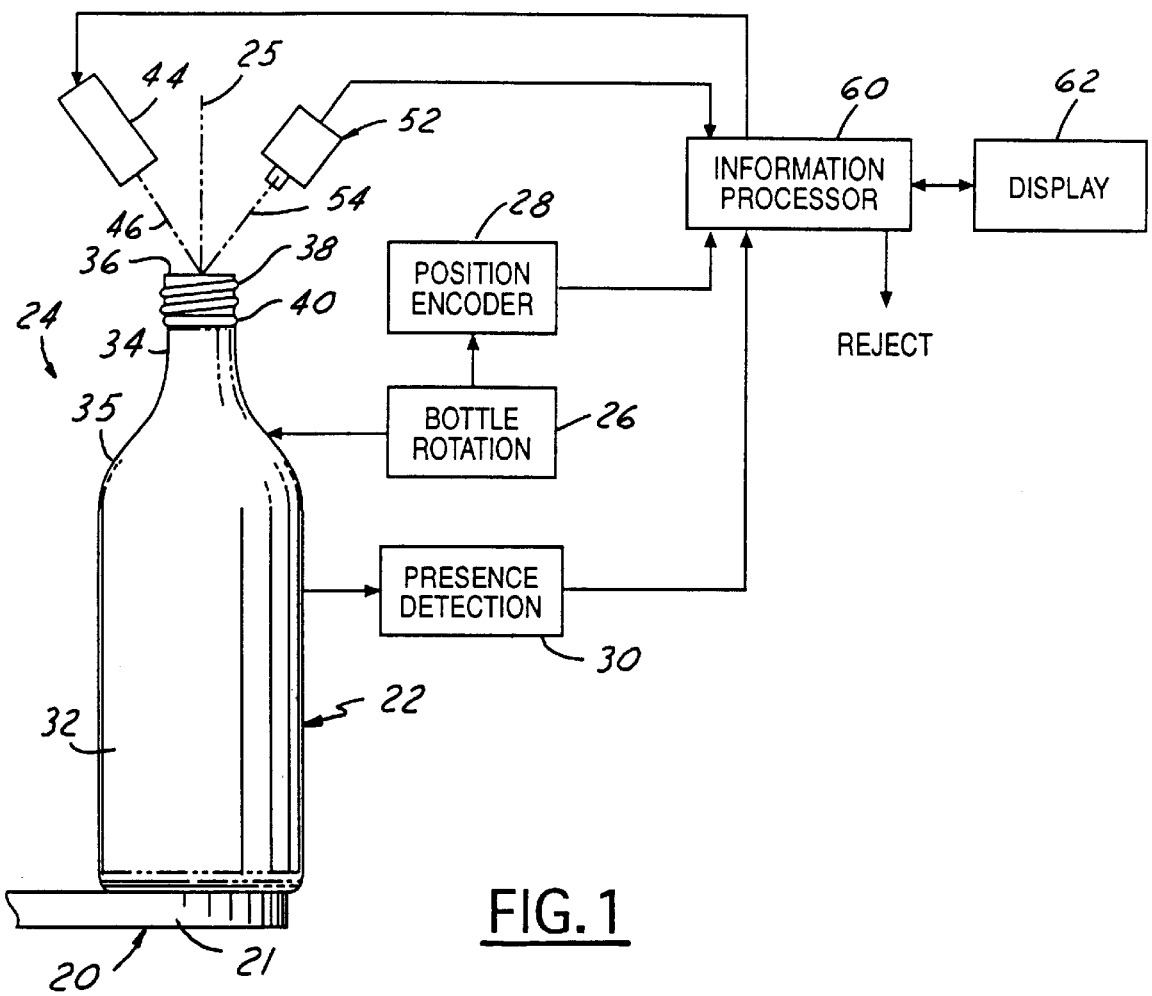
FIG. 1 is a schematic diagram of apparatus for inspecting the sealing surface of a container in accordance with one presently preferred embodiment of the invention.

Referring to FIG. 1, a conveyor 20, typically including a starwheel and a slideplate 21, is so disposed and connected to a source of molded containers as to bring successive containers 22 into position at a sealing surface inspection station 24. Such a starwheel conveyor container inspection arrangement is disclosed, for example, in above-noted U.S. Pat. No. 3,313,409. A bottle-rotating device 26, such as a drive roller, is positioned to engage each container 22 in sequence at station 24, and to rotate the container about its central axis 25 as the container is held in fixed position by the conveyor. An encoder 28 is coupled to the container rotation mechanism to provide signals indicative on increments of angular position. Such container rotation increments may comprise fixed increments of angular position, or fixed time increments as the container is rotated at constant velocity. A detector 30, such as a switch, is positioned to provide a signal indicative of presence of container 22 at station 24.

In the implementation of the present invention illustrated in FIG. 1, container 22 comprises a molded glass bottle having a cylindrical body 32 and a generally cylindrical neck 34 that projects upwardly from the body shoulder 35. The finish portion of the container includes an upper portion of neck 34 that terminates in an axially facing cap sealing surface 36, which is inspected in accordance with the present invention. A helical thread 38 is integrally molded into the outer surface of the finish wall that surrounds the container mouth. and a lip or shoulder 40 is formed on the finish wall outer surface over which a cap skirt may be secured in the usual manner for affixing the cap to the container. A step-down may exist around the inside diameter of sealing surface 36 due to characteristics of the mold in which the container was formed. Excessive height at the step-down becomes a wire-edge. When the wire-edge exceeds the height of the sealing surface 36, it becomes an over-press. A wire-edge or an over-press is undesirable for a number of reasons, and may indicate a problem at the container mold. The embodiment of the invention illustrated in FIG. 1 is directed to a method and apparatus for inspecting height or level at sealing surface 36 (and the step-down). In this connection, it will be appreciated as the description unfolds that the term "sealing surface" in the present application refers to the entire sealing surface area including not only the sealing surface proper 36, but also the step-down.

Figure 2:
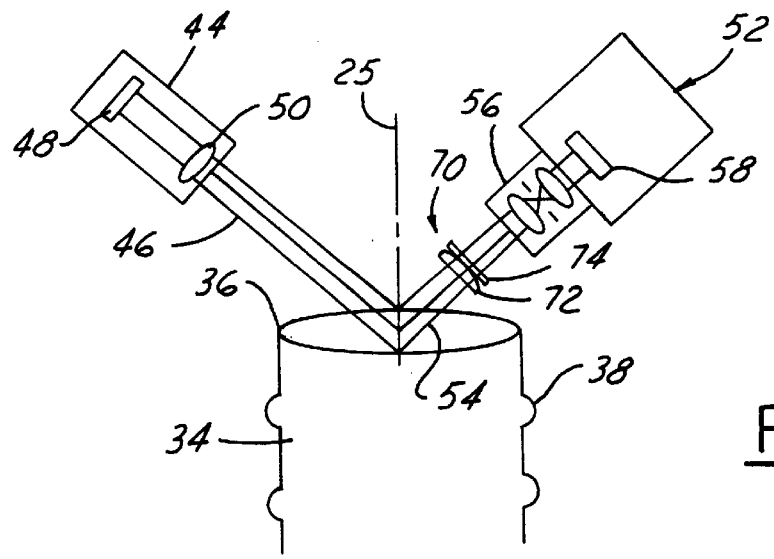
FIG. 2 is a fragmentary schematic diagram that illustrates operation of the embodiment illustrated in FIG. 1.

A light source 44 is positioned above sealing surface 36 of container 22 at station 24, and oriented to direct a narrow collimated beam 46 of light energy downwardly at an acute angle onto sealing surface 36. Specifically, light beam 46 comprises a collimated line-shaped light beam that has a long dimension at sealing surface 36 orthogonal to and (preferably) coplanar with container axis 25 at the nominal position and orientation of container 22 at station 24, and a narrow dimension tangential to the container axis. Referring to FIG. 2, light source 44 is preferably a structured light source that may comprise a laser diode 48 and cylindrical lenses 50 for forming the collimated line-shaped laser beam as described. A camera 52 is positioned above sealing surface 36 of container 22 at station 24, and oriented to receive that portion 54 of beam 46 reflected from sealing surface 36 (and step-down, if any). Camera 52 includes a focusing lens arrangement 56 and (preferably) a linear array light sensor 58 onto which lens 56 focuses reflected light energy 54. Light source 44 and camera 52 are disposed in the plane of incident light beam 46 and reflected light beam 54. The angle of incidence of illumination beam, 46, and the nominal angle of reflection of beam 54, are each at 45° with respect to axis 25, which is to say that beams 46, 54 are at a nominal angle of 90° with respect to each other.

An information processor 60 (FIG. 1) receives signals from detector 30 indicating presence of a container at inspection station 24, and signals from encoder 28 indicative of increments of container rotation. Camera 52 is likewise coupled to information processor 60 for receiving control signals from processor 60, and for providing output signals to the information processor indicative of position of incidence of reflected light energy 54 on sensor 58. Light source 44 is likewise controlled by processor 60. Processor 60 is also connected to a display 62 for displaying image data to an operator, and provides a reject signal to a suitable mechanism for removing unacceptable containers from the conveyor line.

Figure 3:
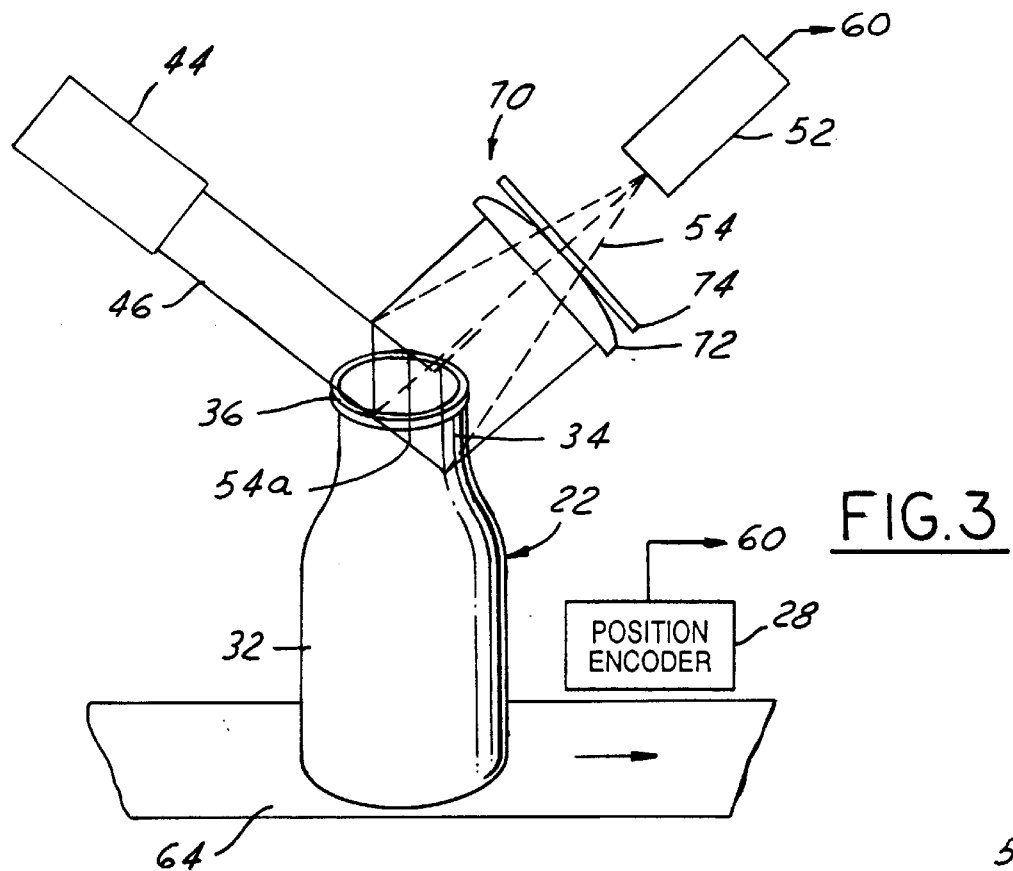
FIG. 3 is a schematic diagram of apparatus for inspecting containers in accordance with the invention at the so-called hot end of the manufacturing process.

In the embodiment of FIGS. 1–2, relative motion between the light source/sensor system and the container is obtained by roller 26 (FIG. 1) or the like that contacts the container and rotates the container about its axis 25. Such a technique is suitable for use at the so-called cold end of a glassware manufacturing process—i.e., downstream of the annealing lehr—where the containers are cool and rigid. However, such a technique would not be suitable for use at the so-called hot end of the manufacturing process—i.e., between the glassware manufacturing machine and the annealing lehr—because the roller would distort the hot and pliable container sidewall. FIG. 3 illustrates a hot container 22 being transported on an endless belt conveyor 64 between the manufacturing machine and the annealing lehr. Position encoder 28 is coupled to conveyor 64 to provide signals to information processor 60 (FIG. 1) indicative of conveyor/container motion, which may be fixed distance increments or fixed time increments during motion at constant speed. Information processor, 60 scans camera 52 at increments of linear container motion so as to obtain multiple images of reflections of light beam 46 from the sealing surface area. For example, camera 52 may be scanned to obtain ten images in which the laser line extends chordally across the sealing surface area. Reflections from the sealing surface area will appear as bright spots against an otherwise dark background. The image within camera 52 preferably extends above and below the nominal height of sealing surface area 36, which will accommodate substantial variations in wobble or height.

In accordance with a specific feature of the present invention, a lens system 70 is positioned between container sealing surface 36 and camera 52 for directing onto sensor 58 of camera 52 only light energy reflected from the container sealing surface area in planes parallel to the common plane of axis 25 and sensor 58. That is, sensor 58 preferably comprises a linear array sensor that has a linear array of CCD sensing elements or pixels disposed in a line coplanar with (and at a nominal 45° angle to) container axis 25 and perpendicular to the long dimension of illumination beam 46. Alternatively, sensor 58 may comprise an area array sensor in which one row or column of pixels is coplanar with axis 25 and monitored to implement the present invention. This modification would be particularly useful if the area array sensor is used to perform other inspection functions. Pixel lines in the sensor not coplanar with the container axis could be used to determine cocked finish variations, as illustrated in FIG. 8.

Figure 4:
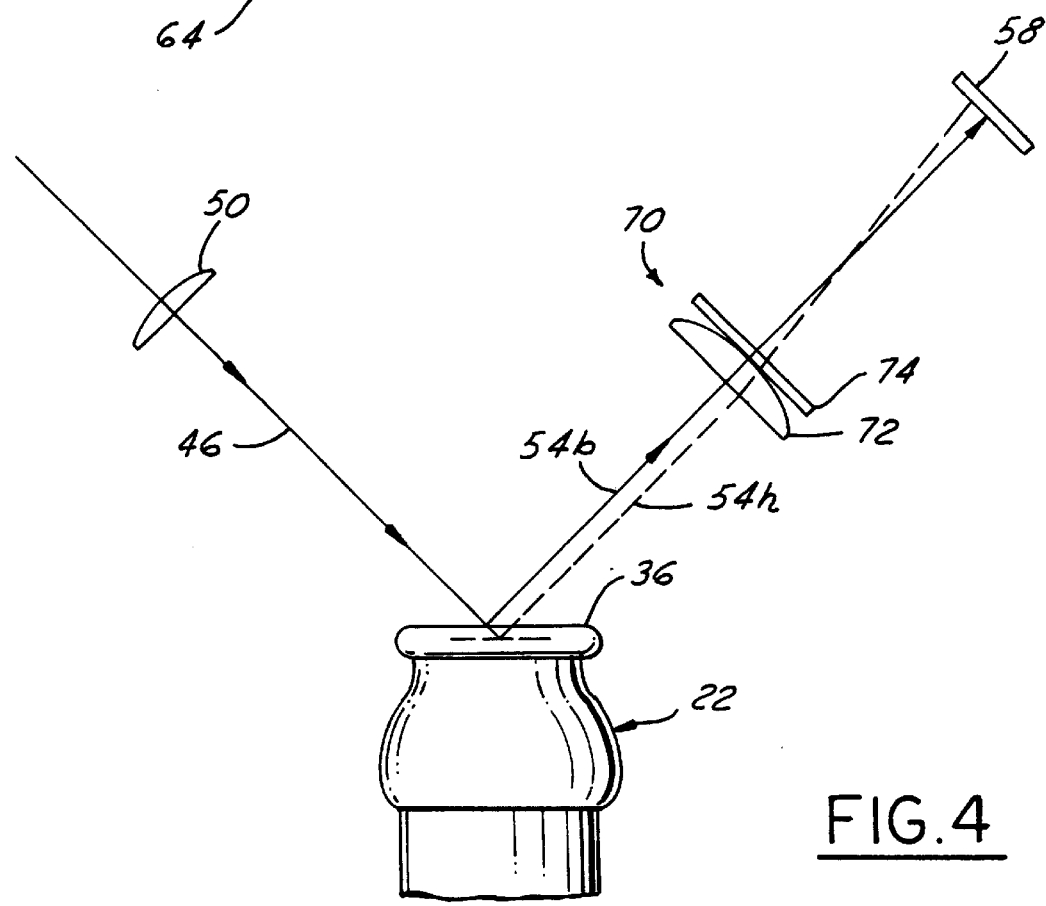

Lens system 70 preferably includes a cylindrical lens 72, and a fresnel or spherical lens 74. Of the light rays in the collimated line-shaped beam that illuminate the sealing surface, only the rays 54a, 54b (FIGS. 4 and 5) reflected form the peak of the sealing surface 36 will be parallel to the plane of axis 25 and sensor 58, while other reflected light rays 54c, 54d and 54e (FIG. 7) will be non-parallel to the plane of axis 25 and sensor 58. Thus, as shown in FIG. 7, these non-parallel rays 54c, 54d and 54e will be directed away from sensor 58, and thus not detected by the sensor. On the other hand, in planes parallel to the container axis, the combination of sensor 58 and lens system 70 functions as a full imaging system so as to gather and direct onto sensor 58 not only light energy 54h reflected from a plane 36a (FIG. 6) parallel to but displaced from the nominal position of sealing surface 36, and thus indicative of a low or high sealing surface, but also light energy 54i, 54j reflected from angulated sealing surfaces 36b and 36c (FIG. 6) are potentially indicative of a warped or cocked sealing surface. It should be noted in FIG. 6 that light rays 54b, 54i, 54j reflected from sealing surface 36, either at the nominal planar position or at cocked positions 36b, 36c, are incident on sensor 58 at the same point as long as the position of incidence of illumination beam 46 is the same. On the other hand, position of incidence on sensor 58 of the light ray 54h reflected from sealing surface position 36a is displaced from such nominal position, indicating a change in apparent height at the sealing surface.

Figure 5:
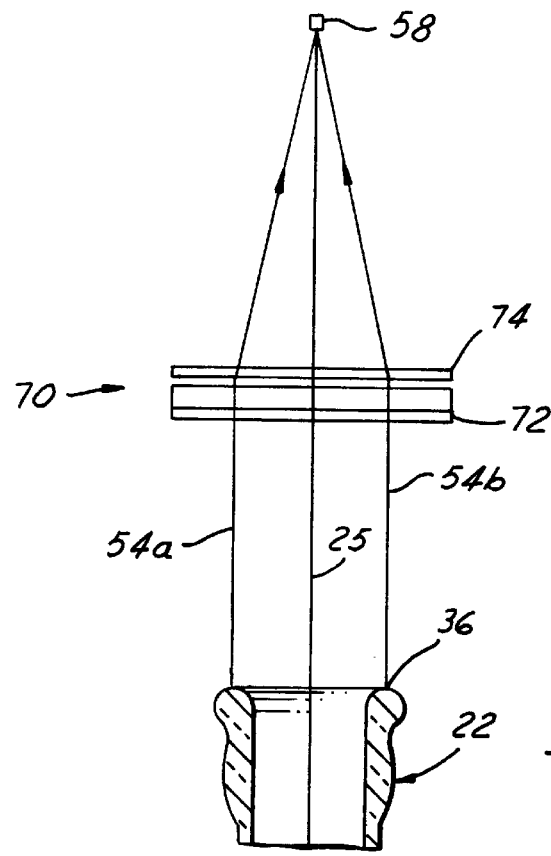
Figure 6:
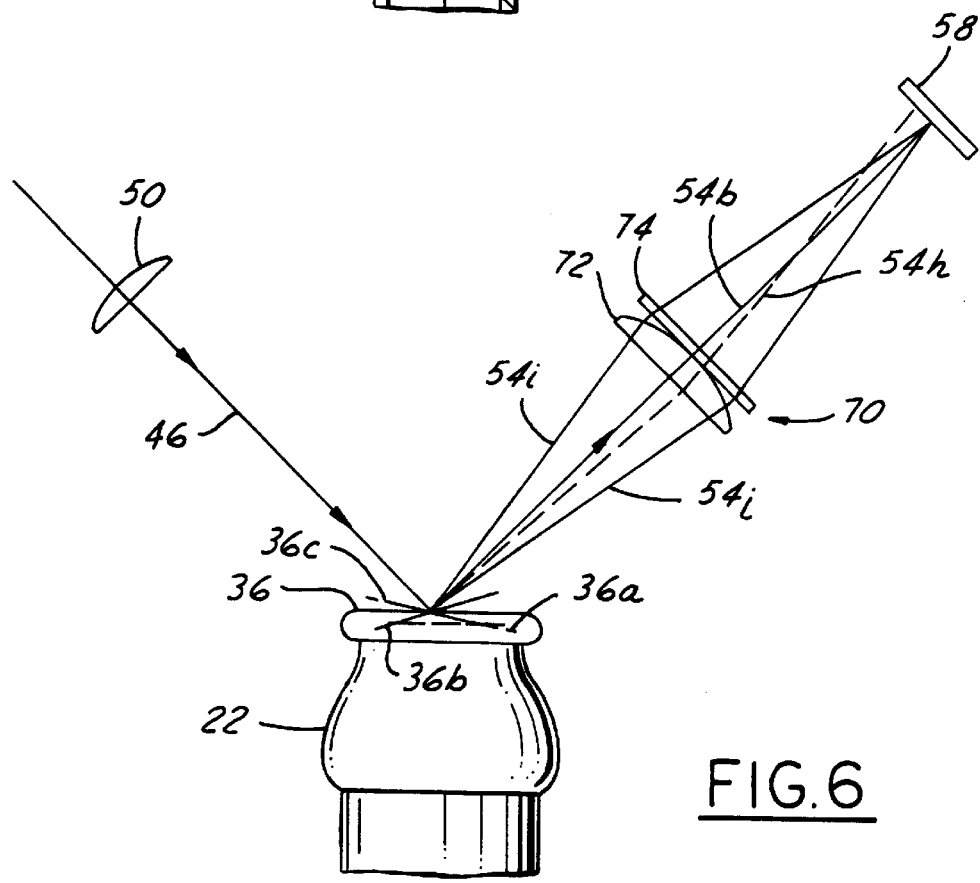

The apparatus of the present invention, including particularly lens system 70, is thus in a sense telecentric in the plane of FIGS. 5 and 7 in the sense that only light rays parallel to container/sensor plane are directed onto the sensor. Placement of array 58 at the focal point of the fresnel or spherical lens 74 effectively selects the entering rays that are parallel to the optical axis, which will be the only rays that cause output from the array. These rays are the rays that reflect from at or near the apex or highest points of the sealing surface area along the line of illumination by the laser beam. Thus, in FIG. 8, the rays 54a, 54b are parallel to each other and parallel to the plane of axis 25 and sensor 58. After refraction by lens system 70, they strike the active area of sensor 58, which is placed at the line of focus of the lens system. On the other hand, light rays 54f and 54g are not parallel to axis 25. After refraction, these light rays are focused at point 54k displaced from sensor 58. Thus, sensor 58 does not respond to reflected light rays 54f and 54g.

Linear array sensor 58 will thus normally preferentially receive light rays from the peaks at chordally opposed sides of sealing surface 36, in the form of two spots of light at the sensor. If these light spots coincide in position, then the chordally opposed sides of the sealing surface are at the same height, with this height being indicated by position of incidence on the sensor. On the other hand, if these light spots do not coincide, then there is a difference in elevation between the two sides of the sealing surface, potentially indicating a warped or cocked sealing surface. Information regarding warp, dip and cock at the sealing surface can be obtained using standard image processing techniques.

There has thus been disclosed an apparatus and method that fully satisfy all of the objects and aims previously set forth. Several alternatives and modifications have been suggested. Other alternatives and modifications will suggest themselves to persons of ordinary skill in the art based upon the detailed description provided. The invention is intended to embrace all such alternatives and modifications as fall within the spirit and broad scope of the appended claims.

What is claimed is:

1. Apparatus for inspecting the finish of a container having a central axis and an open mouth surrounded by an axially facing sealing surface area for sealing engagement with a container cap, said apparatus comprising:

a light source positioned to direct a collimated line-shaped light beam onto the sealing surface area of a container in such a way that the line-shaped light beam is incident entirely across the sealing surface area on both sides of the container axis, having a long dimension orthogonal to the container axis and a narrow dimension tangential to the container axis, light sensor means disposed in a common plane with said axis to receive portions of said line-shaped light beam reflected from the sealing surface area of the container, lens means for directing onto said light sensor means light energy reflected by the container sealing surface area only in planes parallel to said common plane, and means for detecting variations in level at the sealing surface area as a function of position of incidence of the reflected light energy on said light sensor means.

2. The apparatus set forth in claim 1 wherein lens means and said sensor means together comprise a full imaging system only for light energy reflected from said sealing surface in planes parallel to said common plane.

3. The apparatus set forth in claim 2 wherein said light sensor means comprising a linear array sensor of light sensitive elements oriented perpendicular to said long dimension of said line-shaped light beam.

4. The apparatus set forth in claim 3 wherein said lens means comprise a cylindrical lens and a fresnel or spherical lens, and wherein said linear array sensor is positioned at the focal point of said fresnel or spherical lens.

5. The apparatus set forth in claim 1 wherein said variations detecting means includes means for detecting a difference in level between diametrically opposed sides of the container mouth as a function of a difference in position of incidence on said sensor means of reflected light from said diametrically opposed sides.

6. The apparatus set forth in claim 1 further comprising means for holding the container in stationary position beneath said light source and said sensor means, and rotating the container about its axis.

7. The apparatus set forth in claim 1 further comprising means for translating a container beneath said light source and sensor means in a direction orthogonal to said axis.

8. A method of inspecting the finish of a container having a central axis and an open mouth surrounded by an axially facing sealing surface area, said method comprising the steps of:

(a) directing a collimated line-shaped light beam downwardly onto the sealing surface area of a container under inspection such that said line-shaped beam extends chordally across the container sealing surface area and is incident on both sides of the container mouth, (b) directing onto a light sensor light energy reflected from the container sealing surface area only in planes parallel to the container axis, and (c) detecting variations in level at the sealing surface area as a function of position of incidence on said sensor of light energy reflected from both sides of the sealing surface area.

* * * * *